(12) United States Patent
Galeone et al.

(10) Patent No.: US 8,435,559 B2
(45) Date of Patent: May 7, 2013

(54) MICROCAPSULES FROM EMULSION POLYMERIZATION OF TETRAALKOXYSILANE

(75) Inventors: Fabrizio Galeone, Buvrinnes (BE); Arnaud Labrosse, Manage (BE); Leon Marteaux, Brussels (BE); Henri Schirosi, Fosses-la-Ville (BE); Brett Zimmerman, Frankenmuth, MI (US)

(73) Assignee: Dow Corning Corporation, Midland, MI (US)

( * ) Notice: Subject to any disclaimer, the term of this patent is extended or adjusted under 35 U.S.C. 154(b) by 334 days.

(21) Appl. No.: 12/302,338

(22) PCT Filed: Jun. 27, 2007

(86) PCT No.: PCT/US2007/014989
§ 371 (c)(1), (2), (4) Date: Nov. 25, 2008

(87) PCT Pub. No.: WO2008/002637
PCT Pub. Date: Jan. 3, 2008

(65) Prior Publication Data
US 2009/0252809 A1    Oct. 8, 2009

Related U.S. Application Data

(60) Provisional application No. 60/816,738, filed on Jun. 27, 2006.

(51) Int. Cl.
*A61K 9/48* (2006.01)
(52) U.S. Cl.
USPC .......................................................... 424/451
(58) Field of Classification Search .................. None
See application file for complete search history.

(56) References Cited

U.S. PATENT DOCUMENTS

| | | |
|---|---|---|
| 4,880,851 A | 11/1989 | Yamamoto |
| 4,980,392 A | 12/1990 | Yamamoto |
| 4,987,161 A | 1/1991 | Yamamoto |
| 4,988,744 A | 1/1991 | Yamamoto |
| 5,075,350 A | 12/1991 | Yamamoto |
| 5,387,622 A | 2/1995 | Yamamoto |
| 5,395,620 A | 3/1995 | Huc et al. |
| 5,455,048 A | 10/1995 | Lahmani et al. |
| 5,622,656 A | 4/1997 | Huc et al. |
| 5,876,699 A | 3/1999 | DiSomma et al. |
| 6,159,453 A | 12/2000 | Avnir et al. |
| 6,238,650 B1 | 5/2001 | Lapidot et al. |
| 6,251,313 B1 | 6/2001 | Deubzer et al. |
| 6,251,969 B1 | 6/2001 | Worner et al. |
| 6,303,149 B1 | 10/2001 | Magdassi et al. |
| 6,337,089 B1 | 1/2002 | Yoshioka et al. |
| 6,436,375 B1 | 8/2002 | Lapidot et al. |
| 6,468,509 B2 | 10/2002 | Lapidot et al. |
| 2002/0037261 A1 | 3/2002 | Lapidot et al. |
| 2002/0064541 A1 | 5/2002 | Lapidot et al. |
| 2007/0292676 A1 | 12/2007 | Naigertsik et al. |

FOREIGN PATENT DOCUMENTS

| | | |
|---|---|---|
| DE | 19537415 | 4/1997 |
| EP | 1471995 | 7/2008 |
| FR | 2687914 | 9/1993 |
| FR | 2726760 | 5/1996 |
| GB | 2416524 | 2/2006 |
| JP | 2-2867 | 1/1990 |
| JP | 5-178995 | 7/1993 |
| WO | WO 02/20148 | 3/2002 |
| WO | WO 03066209 A1 * | 8/2003 |

OTHER PUBLICATIONS

G. Berset & H. Gonzenbach (COLIPA Task force); Proposed Protocol for Determination of Photostability, Part I: Cosmetic UV-filters, Int. J.Cosmet.Sci. 18, 167-188 (1996).

* cited by examiner

*Primary Examiner* — Paul Dickinson
(74) *Attorney, Agent, or Firm* — Alan Zombeck

(57) ABSTRACT

A process is disclosed for preparing microcapsules having a shell thickness of at least 18 nanometers by polymerizing a tetraalkoxysilane at the oil/water interface of an emulsion containing 0.1 to 0.3 weight percent of a cationic surfactant. The microcapsules are useful to prepare encapsulated sunscreens having sufficient robustness to prevent leakage of the encapsulated sunscreen in a formulated composition.

4 Claims, No Drawings

MICROCAPSULES FROM EMULSION POLYMERIZATION OF TETRAALKOXYSILANE

CROSS REFERENCE TO RELATED APPLICATIONS

This application is a U.S. national stage filing under 35 U.S.C. §371 of PCT Application No. PCT/US07/014989 filed on Jun. 27, 2007, currently pending, which claims the benefit of U.S. Provisional Patent Application No. 60/816,738 filed Jun. 27, 2006 under 35 U.S.C. §119(e). PCT Application No. PCT/US07/014989 and U.S. Provisional Patent Application No. 60/816,738 are hereby incorporated by reference.

TECHNICAL FIELD

This invention relates to a process for preparing microcapsules having a shell thickness of at least 18 nanometers by polymerizing a tetraalkoxysilane at the oil/water interface of an emulsion containing 0.1 to 0.3 weight percent of a cationic surfactant. The microcapsules are useful to prepare encapsulated sunscreens having sufficient robustness to prevent leakage of the encapsulated sunscreen in a formulated composition.

BACKGROUND

Various encapsulation techniques have been described in the art as a manner for protecting and delivering cosmetic/pharmaceutical actives. In particular, there is widespread interest to encapsulate sunscreen actives to ensure their protection in a formulated product, and to minimize skin penetration upon application. A significant problem with current sunscreens is their potential interaction in a formulated product leading to a reduction of their UV absorbance activity. One way to prevent the interactions is to isolate the sunscreen by encapsulating one or more sunscreen agent and composition thereof. Representative examples of microcapsules containing UV sunscreens are disclosed in FR2 642 329, DE-A 195 37 415, EP-A 509 904, FR 2 726 760 and FR 2 687 914 as well as WO 00/71084, U.S. Pat. No. 6,303,149, WO 98/31333, U.S. Pat. No. 5,876,699 and WO 00/72806.

JP-A-2-2867 describes sunscreen benzophenone derivatives encapsulated in fine spherical silica particles. The sunscreen is dissolved in aqueous alkali metal silicate solution and is emulsified in an organic non-solvent to form a water-in-oil emulsion. The emulsion is acidified to form a water-insoluble precipitate of sunscreen encapsulated in silica. The process of JP-A-2-2867 is suitable for hydrophilic sunscreen active materials, but most sunscreen active materials are lipophilic.

WO-A-98/31333 describes sunscreen-doped sol-gel materials and a method for their preparation comprising condensation polymerising a metal or semi-metal alkoxide or ester in the presence of at least one sunscreen ingredient, resulting in the entrapment of the sunscreen ingredients within the formed sol-gel matrix.

U.S. Pat. No. 6,303,149 describes a process for preparing sol-gel microcapsules loaded with functional molecules by emulsifying sol-gel precursors and the functional molecules in an aqueous solution, and mixing the emulsion with an acidic, neutral or basic aqueous solution to obtain a suspension of microcapsules. This sol-gel process described is a multiple kettle process requiring removal of the continuous phase.

U.S. Pat. No. 6,238,650 describes a sunscreen composition comprising at least one sunscreen active ingredient and a cosmetically acceptable vehicle, wherein said sunscreen active ingredient is in the form of sol-gel microcapsules containing at least one sunscreen compound. The sol-gel microcapsules are prepared by the method disclosed in U.S. Pat. No. 6,303,149.

EP-A-281034 describes a perfume encapsulated and/or clathrated in a matrix of inorganic polymer prepared from a metal alkoxide such as tetraethyl orthosilicate (TEOS). An aqueous dispersion or solution of perfume and TEOS is treated with an acid catalyst to cause hydrolysis, then with a base catalyst to cause polymerisation to a gel.

EP-A-941761 describes a process for preparing microcapsules with an organopolysiloxane shell and a core material, in which the shell is formed in situ by hydrolysis and polycondensation of an organosilane and/or a condensation product thereof having at most 4 silicon atoms.

JP-51-78995-A describes dispersing a silyl-treated pigment with TEOS in acetone and adding to ammoniacal aqueous ethanol with stirring to form a micropowder of particles having a pigment core.

EP-A-934773 describes microcapsules whose capsule wall comprises organopolysiloxane synthesised by polycondensing a compound of the formula $R_nSi(OH)_mY_{(4-m-n)}$ where m=1-4; n=0-3; R represents an organic group with a C atom directly bonded to a SI atom; and Y is an alkoxy group, H or a siloxy group.

WO-A-00/71084 describes preparing a sunscreen composition with improved photostability that contains at least two sunscreen actives which are photo-unstable when formulated together by microencapsulating at least one of the actives and adding other components of the sunscreen composition.

WO-A-01/80823 describes a therapeutic or cosmetic composition comprising microcapsules of diameter 0.1-100μ having a core-shell structure. The core includes at least one active. The shell comprises an inorganic polymer obtained by a sol-gel process, and releases the active after topical application.

WO-A-03/066209 describes a process of making lipophilic cosmetic, chemical, or pharmaceutical active material compositions encapsulated within a shell obtained from the emulsion polymerisation products of tetraalkoxysilane. The process of making these microcapsules is a one kettle process without removal of the continuous phase.

WO-A-2005/009604 describes a process of making core-shell microcapsules wherein the shell comprises at least one inorganic polymer comprising polymerized precursors obtained by in-situ polymerization of the precursors; wherein the concentration of the core material based total weight of the microcapsules is above 95% w/w.

WO-A-03/066209 describes a new encapsulation process by ex-situ emulsion polymerization from tetraalkoxysilanes and the surfactant concentration in the starting cationic emulsion.

There is a need for encapsulated sunscreens in a form in which the encapsulating shell is sufficiently robust to prevent leakage of the sunscreen into the formulation composition where antagonistic effects can occur. Furthermore, it is desirable to prevent skin contact and penetration of the sunscreen. The problem of leakage is particularly severe with cinnamic ester derivatives such as 2-ethylhexyl methoxycinnamate also known as EHMC or OMC or Parsol® MCX. EHMC is known to be a useful UV B absorber but that compound can cause unwanted effects, e.g. allergic reactions, and they have also a significant cross-reactivity with other sunscreen agents in particular with butylmethoxydibenzoylmethane.

The present inventors have discovered an improved process for preparing microcapsules using an "ex-situ emulsion polymerization" of tetraalkoxysilanes. In particular, the present inventors have discovered the combination of two process parameters during ex-situ emulsion polymerization results in the production of microcapsules having improved formulation integrity and performance. These parameters involve controlling the amount of cationic surfactant present in the process and the overall shell thickness of the micro capsule.

SUMMARY

This invention provides a process for preparing microcapsules comprising;
I) mixing an oil phase and an aqueous solution of a cationic surfactant to form an oil in water emulsion,
II) adding a water reactive silicon compound comprising a tetraalkoxysilane to the oil in water emulsion,
III) polymerizing the tetraalkoxysilane at the oil/water interface of the emulsion to form a microcapsule having a core containing the oil and a shell,
wherein the weight % of cationic surfactant to the oil phase in the emulsion of step I) ranges from 0.1% to 0.3% and the shell thickness of the microcapsule is at least 18 nanometers.

This invention also relates to the microcapsules, and suspensions of the microcapsules, prepared according to present process.

The present invention further provides microcapsules, and suspensions thereof, having a particle size ranging from 0.2 to 10 micrometers comprising;
A) a shell comprising a silicon-based polymer prepared from polymerizing a tetraalkoxysilane,
B) an oil phase core,
wherein the weight ratio of the oil phase core to the shell is greater than 10/1, and the shell has a thickness of at least 18 nanometers.

The microcapsules are particularly useful to prepare encapsulated sunscreens having sufficient robustness to prevent leakage of the encapsulated sunscreen into a formulated composition containing other sunscreens. Therefore, antagonistic effects that limit shelf storage of the formulated composition are minimized using the present encapsulated sunscreens.

DETAILED DESCRIPTION

The first step of the present process involves mixing an oil phase and an aqueous solution of a cationic surfactant to form an oil in water emulsion.
The Oil Phase As used herein, "oil phase" encompasses any compound, or mixture of compounds that is hydrophobic. Typically, the oil phase is liquid when forming the oil in water emulsion. The oil phase may contain any organic, silicone, or fluorocarbon based oil, either alone or in combination. The oil phase may also contain any solvent or diluent, which may be added for the purpose of solubilizing solid hydrophobic compounds to create a liquid oil phase during formation of the emulsion.

In one embodiment of the present invention, the oil phase contains a sunscreen agent. The sunscreen agents which are used in this embodiment can be liquid sunscreens and blends thereof. In the same embodiment of this invention solid organic sunscreens can be solubilised in a good solvent before encapsulation. Sunscreen agents in this invention might be for example DEA-methoxycinnamate, diethylhexylbutamido triazine, diisopropyl methyl cinnamate, 1-(3,4-dimethoxyphenyl)-4,4-dimethyl-1,3-pentanedione, drometrizole trisiloxane, benzophenone-3, benzophenone-4,3-benzylidene camphor, 3-benzylidene camphor sulfonic acid, bis-ethylhexyloxyphenol methoxyphenyl triazine, butyl methoxydibenzoylmethane, camphor benzalkonium methosulfate, ethyl diisopropylcinnamate, 2-ethylhexyl dimethoxybenzylidene dioxoimidazolidine propionate, ethylhexyl dimethyl PABA, ethylhexyl salicilate, ethylhexyl triazone, ethyl PABA, homosalate, isoamyl p-methoxycinnamate, menthyl anthranilate, 4-methylbenzylidene camphor, methylene-bisbenzotriazolyl tetramethylbutylphenol, octocrylene, PABA, phenylbenzimidazole sulfonic acid, polyacrylamidomethyl benzylidene camphor, polysilicone-15, potassium phenylbenzimidazole sulfonate, sodium phenylbenzimidazole sulfonate, TEA-salicilate, terephtalidene dicamphor sulfonic acid, 2,2-(1,4-phenilene)bis-(1H-benzimidazole-4,6-disulfonic acid, 2-(4-diethylamino-2-hydroxy-benzoyl)-benzoic acid hexylester but is not limited to this list of UV absorber.

Other examples of active materials which may be used in the oil phase of the present process include UV absorbers used in coatings, paints, plastics materials, sealants or textile finishes for improving weatherability and resisting fading.

The oil phase may contain other components such as a silicone, organic, or personal care actives that are substantially soluble with the other oil phase components, and conversely, is substantially insoluble in water. Thus, other typical emollient components can include: silicones, such as volatile siloxanes, polydimethylsiloxane fluids, high molecular weight (i.e. $M_n$>1000) siloxanes, including silicone elastomers and resins; organic compounds such as, hydrocarbon oils, waxes, emollients, fragrances or perfume compositions; and personal care organic actives such as vitamins.
Cationic Surfactant The oil phase is mixed with an aqueous solution of a cationic surfactant to form an oil in water emulsion.

Cationic surfactants useful in this invention might be quaternary ammonium hydroxides such as octyl trimethyl ammonium hydroxide, dodecyl trimethyl ammonium hydroxide, hexadecyl trimethyl ammonium hydroxide, octyl dimethyl benzyl ammonium hydroxide, decyl dimethyl benzyl ammonium hydroxide, didodecyl dimethyl ammonium hydroxide, dioctadecyl dimethyl ammonium hydroxide, tallow trimethyl ammonium hydroxide and coco trimethyl ammonium hydroxide as well as corresponding salts of these materials, fatty amines and fatty acid amides and their derivatives, basic pyridinium compounds, quaternary ammonium bases of benzimidazolines and polypropanolpolyethanol amines but is not limited to this list of cationic surfactants. Alternatively, the cationic surfactant is cetyl trimethyl ammonium chloride.

For purposes of this invention, the cationic surfactant may be selected from an amphoteric surfactant such as cocamidopropyl betaine, cocamidopropyl hydroxysulfate, cocobetaine, sodium cocoamidoacetate, cocodimethyl betaine, N-coco-3-aminobutyric acid and imidazolinium carboxyl compounds but is not limited to this list of amphoteric surfactants.

The above surfactants may be used individually or in combination. The cationic or amphoteric surfactant is dissolved in water and the resulting aqueous solution used as a component in aqueous or continuous phase of the oil in water emulsion of step I).

Although not wishing to be bound by any theory, the present inventors believe the use of a cationic or amphoteric surfactant promotes condensation and polymerisation of the tetraalkoxysilane at the interface of the emulsified droplets of the sunscreen agent composition, leading to non-diffusive microcapsules. The tetraalkoxysilane hydrolyzes and condenses upon reacting in the emulsion. The anionically charged hydrolysis product is attracted to the cationic or amphoteric surfactant at the interface where it forms the silicon based polymer shell.

The concentration of the cationic surfactant during the formation of the oil in water emulsion should be between 0.1% and 0.3% by weight of the oil phase concentration used. We have found that the use of low levels of cationic or amphoteric surfactant during emulsification of the oil phase and reaction with the alkoxysilane leads to microcapsules which are more resistant to diffusion or leaching of the oil phase from the microcapsules.

Auxillary surfactants, and in particular nonionic surfactants, may be added during the formation of the oil in water emulsion. Suitable non-ionic surfactants are; polyoxyalkylene alkyl ethers such as polyethylene glycol long chain (12-14C) alkyl ether, polyoxyalkylene sorbitan ethers, polyoxyalkylene alkoxylate esters, polyoxyalkylene alkylphenol ethers, ethylene glycol propylene glycol copolymers, polyvinyl alcohol and alkylpolysaccharides, for example materials of the structure $R^1$—O—$(R^2O)_m$-$(G)_n$ wherein $R^1$ represents a linear or branched alkyl group, a linear or branched alkenyl group or an alkylphenyl group, $R^2$ represent an alkylene group, G represents a reduced sugar, m denotes 0 or a positive integer and n represent a positive integer as described in U.S. Pat. No. 5,035,832 but is not limited to this list of non-ionic surfactants.

The aqueous solution of the cationic or amphoteric surfactant may contain additional/optional components, providing they are water soluble. For example a water-miscible organic solvent such as an alcohol or lactam may be added. Furthermore, other water soluble ingredients that are commonly used in personal care formulations, may be added to the aqueous phase. Such ingredients include additional surfactants, thickeners, preservatives, antimicrobial, and water soluble actives and fragrances.

The oil phase and aqueous solution of the cationic or amphoteric surfactant are mixed together to form an oil in water emulsion. Mixing and emulsion formation may occur using any known techniques in the emulsion art. Typically, the oil phase and aqueous solution of the cationic or amphoteric surfactant are combined using simple stirring techniques to form an emulsion. Particle size of the oil in water emulsion may then be reduced before addition of the tetraalkoxysilane by any of the known in the art emulsification device. Useful emulsification devices in this invention can be homogenizer, sonolator, rotor-stator turbines, colloid mill, microfluidizer, blades, helix and combination thereof but is not limited to this list of emulsification devices. This further processing step reduces the particle size of the starting cationic oil in water emulsion to values ranging from 0.2 to 500 micrometers, with typical particle sizes ranging between 0.5 micrometers and 100 micrometers.

The weight ratio of oil phase to aqueous phase in the emulsion can generally be between 40:1 and 1:50, although the higher proportions of aqueous phase are economically disadvantageous particularly when forming a suspension of microcapsules. Usually the weight ratio of oil phase to aqueous phase is between 2:1 and 1:3. If the oil phase composition is highly viscous, a phase inversion process can be used in which the oil phase is mixed with surfactant and a small amount of water, for example 2.5 to 10% by weight based on the oil phase, forming a water-in-oil emulsion which inverts to an oil-in-water emulsion as it is sheared. Further water can then be added to dilute the emulsion to the required concentration.

Adding and Polymerizing the Tetraalkoxysilane at the Oil/Water Interface of the Emulsion The second and third steps of the present process involve adding a water reactive silicon compound comprising tetraalkoxysilane to the oil in water emulsion, and polymerizing the tetraalkoxysilane at the oil/water interface of the emulsion. Although not wishing to be bound by any theory, the present inventors believe the third step of the present process effects an "ex-situ emulsion polymerization" by which the tetraalkoxysilane precursor hydrolyzes and condenses at the oil/water interface leading to the formation of core-shell microcapsules via a phase transfer of the precursors.

The tetraalkoxysilane, such as tetraethoxysilane (TEOS), can be used in monomeric form or as a liquid partial condensate. The tetraalkoxysilane can be used in conjunction with one or more other water-reactive silicon compound having at least two, preferably at least 3, Si—OH groups or hydrolysable groups bonded to silicon, for example an alkyltrialkoxysilane such as methyltrimethoxysilane or a liquid condensate of an alkyltrialkoxysilane. Hydrolysable groups can for example be alkoxy or acyloxy groups bonded to silicon. The water reactive silicon compound can for example comprise 75-100% by weight tetraalkoxysilane and 0-25% trialkoxysilane. The alkyl and alkoxy groups in the tetraalkoxysilanes or other silanes preferably contain 1 to 4 carbon atoms, most preferably 1 or 2 carbon atoms. The tetraalkoxysilane, and other water-reactive silicon compound if used, hydrolyses and condenses to form a network polymer, that is a 3-dimensional network of silicon-based material, around the emulsified droplets of the lipophilic active material composition. The water-reactive silicon compound preferably consists of at least 75%, and most preferably 90-100% tetraalkoxysilane. We have found that a tetraalkoxysilane effectively forms impermeable microcapsules, forming a 3-dimensional network consisting substantially of $SiO_{4/2}$ units.

The tetraalkoxysilane, and other water reactive silicon compound if used, can be added to the emulsion of active material composition as an undiluted liquid or as a solution in an organic solvent or in an emulsion form. The tetraalkoxysilane and the oil in water emulsion are mixed during addition and subsequent polymerization to form the silicon-based polymer shell on the surface of the emulsified droplets. Mixing is typically effected with stirring techniques. Common stirring techniques are typically sufficient to maintain the particle size of the starting oil in water emulsion while allowing the tetraalkoxysilane to polymerize and condense at the oil water interface The amount (based on weight) of tetraalkoxysilane added in step II typically ranges from 6/1 to 1/13, or alternatively from 1/3.6 to 1/6.1, based on the weight amount of oil phase present in the emulsion.

The polymerization of the tetraalkoxysilane at the oil/water interface typically is a condensation reaction which may be conducted at acidic, neutral or basic pH. The condensation reaction is generally carried out at ambient temperature and pressure, but can be carried out at increased temperature, for example up to 95° C., and increased or decreased pressure, for example under vacuum to strip the volatile alcohol produced during the condensation reaction.

Any catalyst known to promote the polymerization of the tetraalkoxysilane may be added to step III to form the shell of the microcapsule. The catalyst is typically an oil soluble organic metal compound, for example an organic tin compound, particularly an organotin compound such as a diorganotin diester, for example dimethyl tin di(neodecanoate), dibutyl tin dilaurate or dibutyl tin diacetate, or alternatively a tin carboxylate such as stannous octoate, or an organic titanium compound such as tetrabutyl titanate. An organotin catalyst can for example be used at 0.05 to 2% by weight based on the tetraalkoxysilane. An organotin catalyst has the advantage of effective catalysis at neutral pH. The catalyst is typically mixed with the oil phase components before it is emulsified, since this promotes condensation of the tetraalkoxysilane at the surface of the emulsified oil phase droplets. A catalyst can alternatively be added to the emulsion before the addition of the tetraalkoxysilane, or simultaneously with the tetraalkoxysilane, or after the addition of the tetraalkoxysilane to harden and make more impervious the shell of silicon-based polymer which has been formed. Encapsulation can however be achieved without catalyst. The catalyst, when used, can be added undiluted, or as a solution in an organic solvent such as a hydrocarbon, alcohol or ketone, or as a mutiphasic system such as an emulsion or suspension.

The polymerization reaction in step III) is allowed to proceed so as to form the shell of a microcapsule that is at least 18 nanometers thick, alternatively the shell has a thickness in the range of 18 to 150 nanometers, alternatively from 18 to 100 nanometers.

Shell thicknesses may be determined from the particle size (PS) of the resulting microcapsules in suspension and the amounts of the oil phase and tetraalkoxysilane used in the process to prepare them according to the following:

$$\text{Shell Thickness (nm)} = [(PS/2) - [(PS/2)*(\text{Payload}/100)^{1/3}]]*1000$$

where PS is particle size (Dv 0.5) expressed in micrometers
payload=Volume oil phase*100/(Volume oil phase+Volume shell)
Volume oil phase=Mass oil phase/density of oil phase
Volume shell=Mass shell/density of the shell This equation is based on the spherically shaped microcapsules having an average diameter as determined by their average particle size (Dv 0.5). Thus, the shell thickness is the difference between the radius of the microcapsule and the radius of the core material in the microcapsule.

$$\text{Shell thickness} = r_{microcapsule} - r_{core}$$

where $r_{microcapsule} = (PS)/2$
and $r_{core} = (PS/2)*(\text{Payload}/100)^{1/3}$ Payload represents the percentage of the microcapsule occupied by the core material, as determined by the amount of oil phase present in the emulsion. Thus, payload is calculated by the relationship;

$$\text{Payload} = \text{Volume oil phase}*100/(\text{Volume oil phase} + \text{Volume shell})$$

The volume oil phase=mass oil phase/density of oil phase. The mass of the oil phase in this equation is the same as the amount used in the process (as per step I) to prepare the microcapsules. In one embodiment of the present invention, the oil phase is ethylhexy methoxycinnamate (EHMC) having a density of 1.011 g/mL.

The volume of the shell=mass of shell/density of silica. The silicon based polymer comprising the shell is expected to have an average chemical composition with the empirical formula $SiO_2$. Thus, the density of the shell is estimated to be 2 g/mL, which approximates the density of silica ($SiO_2$). The mass of the shell is calculated from the amount of tetraalkoxysilane added to the process (as per step II). More specifically, the mass of the shell is based on the expected stoichiometric yield of silicon based polymer of empirical formula $SiO_2$ given the type and amount of the tetraalkoxysilane used in the process. In one embodiment, the tetraalkoxysilane is tetraethoxysilane (TEOS) having a density of 0.934 g/mL. In this embodiment, the assumed complete hydrolysis and condensation of 1 g of TEOS produces 0.288 g of $SiO_2$ polymer (silica).

The formed microcapsules from step III typically remain in suspension. The aqueous continuous phase may contain water miscible organic solvent; for example it usually contains an alcohol such as ethanol generated by hydrolysis of Si-bonded alkoxy groups. It may be advantageous to use the suspension of microcapsules in a water based preparation, for example a cosmetic, chemical or pharmaceutical product without separating the microcapsules from the suspension. In particular, a suspension of encapsulated sunscreen can be incorporated directly into a sunscreen lotion or cream or can even be used itself as a sunscreen lotion. The suspension of encapsulated sunscreen can be used in conjunction with other sunscreens, if desired. For example, an encapsulated UV-B absorber such as octyl methoxycinnamate can be formulated with a UV-A absorber such as avobenzone and optionally with other sunscreens. The UV-A absorber in such a formulation can be free or encapsulated.

For many uses it may be desired to recover the microcapsules from suspension, for example for subsequent dispersion in a different medium. An encapsulated sunscreen can for example be dispersed in a water based cosmetic preparation, typically in such a proportion that the content of sunscreen in the cosmetic preparation is 0.1 to 10% by weight. Alternatively the microcapsules can be redispersed in an organic solvent, optionally with additives such as surfactant and/or polymer. Recovery of the microcapsules can be achieved by any known liquid removal technique, for example by spray drying, spray chilling, filtering, oven drying or lyophilisation.

The present invention thus further relates to the microcapsule suspension, and isolated microcapsules, as prepared according to the processes as described above.

The present invention further provides microcapsules, and aqueous suspensions thereof, having a particle size ranging from 0.2 to 10 micrometers comprising;
A) a shell comprising a silicon-based polymer prepared from polymerizing a tetraalkoxysilane,
B) an oil phase core,
wherein the weight ratio of the oil phase core to the shell is greater than 10/1, alternatively 50/1, alternatively greater than 90/1 and the shell has a thickness of at least 18 nanometers. Such microcapsules and suspensions thereof are obtainable via the processes described above. However, alternative processes may be used.

Sunscreen agent composition can perform their function of screening out harmful UV radiation while they are encapsulated. The silicon-based polymer forming the shell of the microcapsules does not absorb UV and has no negative impact on the sunscreen agent efficiency, and may potentially improve the protection against photodegradation.

Microcapsules according to the invention containing sunscreen agent compositions have good skin adhesion. The microcapsules minimise contact between the sunscreen agent composition and the skin, resulting in decreased penetration and consequently less potential irritation and allergy. The suspension of microcapsules can have a high concentration of sunscreen (high payload) compared to an aqueous dispersion of sunscreen agent, increasing the ease of use of lipophilic sunscreen agent in surfactant based product and allowing the sunscreen agent preparation to have a very liquid product form, which may be sprayed. Encapsulation eliminates the greasy feel associated with lipophilic sunscreens agents, increasing the acceptability and use in skin care products. The microcapsule has little or no effect on the photostability of the encapsulated sunscreen agent. The silicon-based polymer forming the shell of the microcapsules generally remains water insoluble even in the presence of surfactant, so that the encapsulated cosmetic active can be used in water based toiletry preparations including surfactant based products such as hair shampoo, conditioner or colorant, soap bar, lipsticks, mascaras, textile softener, detergent or shower gel.

Alternative uses of encapsulated sunscreens according to the invention are in fabric treatment, for example the suspension of microcapsules or the separated microcapsules can be incorporated in a fabric softener to inhibit subsequent colour fading of the fabric, or in plastics compositions or coatings which are designed to be exposed to sunlight or UV light in use.

EXAMPLES

These examples are intended to illustrate the invention to one of ordinary skill in the art and should not be interpreted as limiting the scope of the invention set forth in the claims. All measurements and experiments were conducted at 23° C., unless indicated otherwise.

The process of the present invention was used in the following examples to prepare suspensions of microcapsules containing a sunscreen, ethylhexy methoxycinnamate (EHMC) (Parsol MCX®). EHMC was selected as a representative core component of the microcapsule (or oil phase component of the starting oil in water emulsion) to demonstrate the utility and robustness of the formed microcapsules prepared according to the process of the present invention. EHMC was selected because of its reactivity (and hence decline in UV absorbance and sunscreen utility) with many other compounds. In particular, ethylhexy methoxycinnamate (EHMC) will react upon irradiation with butylmethoxydibenzoylmethane (BMDBM) via a photochemical interaction to form 1:1 addition product. This results in a loss of the absorption potential, which can be measured by UV spectroscopy. This photoreaction is therefore useful to identify any diffusion of EHMC out of the microcapsules. By measuring the recovery of BMDBM and EHMC, the efficiency of the sunscreen agent retention inside the microcapsules can be determined.

In the following examples the photostability of the suspensions was determined initially and after storage at 43° C. for several weeks according to the method described by G. Berset & H. Gonzenbach (COLIPA Task force); *Proposed Protocol for Determination of Photostability, Part I: Cosmetic UV-filters*, Int. J. Cosmet. Sci. 18, 167-188 (1996), using Atlas Suntest XLS+. The irradiation time was 5.5 h.

Example 1

350 g EHMC (Parsol MCX®) was emulsified in 540.9 g water containing 1.4 g Pareth-3 nonionic polyethylene glycol lauryl ether surfactant and 0.9 g cetyl trimethyl ammonium chloride (CTAC) cationic surfactant. CTAC/EHMC ratio was then 0.25%. The coarse emulsion was passed once through a "Rannie Mini Lab 8.30H" homogeniser operating at 100 bars (10 MPa). 10.46% TEOS was added to the emulsion while stirring to form a coarse emulsion of microcapsules. Microcapsules of average volume particle size (Dv 0.5) 3.05 micrometers were produced in suspension.

Example 2

350 g EHMC (Parsol MCX®) was emulsified in 540.9 g water containing 1.4 g Pareth-3 nonionic polyethylene glycol lauryl ether surfactant and 0.9 g cetyl trimethyl ammonium chloride (CTAC) cationic surfactant. CTAC/EHMC ratio was then 0.25%. The coarse emulsion was passed once through a "Rannie Mini Lab 8.30H" homogeniser operating at 100 bars (10 MPa). 10.46% TEOS was added to the emulsion while stirring to form a coarse emulsion of microcapsules. Microcapsules of average volume particle size (Dv 0.5) 3.55 micrometers were produced in suspension.

Example 3

350 g EHMC (Parsol MCX®) was emulsified in 540.9 g water containing 1.4 g Pareth-3 nonionic polyethylene glycol lauryl ether surfactant and 0.9 g cetyl trimethyl ammonium chloride (CTAC) cationic surfactant. CTAC/EHMC ratio was then 0.25%. The coarse emulsion was passed once through a "APV Model 1000" homogeniser operating at 40 bars (4 MPa). 10.46% TEOS was added to the emulsion while stirring to form a coarse emulsion of microcapsules. Microcapsules of average volume particle size (Dv 0.5) 3.94 micrometers were produced in suspension.

Example 4

350 g EHMC (Parsol MCX®) was emulsified in 540.9 g water containing 1.4 g Pareth-3 nonionic polyethylene glycol lauryl ether surfactant and 0.9 g cetyl trimethyl ammonium chloride (CTAC) cationic surfactant. CTAC/EHMC ratio was then 0.25%. The coarse emulsion was passed once through a "APV Model 1000" homogeniser operating at 40 bars (4 MPa). 10.46% TEOS was added to the emulsion while stirring to form a coarse emulsion of microcapsules. Microcapsules of average volume particle size (Dv 0.5) 4.15 micrometers were produced in suspension.

Example 5

350 g EHMC (Parsol MCX®) was emulsified in 540.9 g water containing 1.4 g Pareth-3 nonionic polyethylene glycol lauryl ether surfactant and 0.9 g cetyl trimethyl ammonium chloride (CTAC) cationic surfactant. CTAC/EHMC ratio was then 0.25%. The coarse emulsion was passed once through an "APV Model 1000" homogeniser operating at 40 bars (4 MPa). 10.46% TEOS was added to the emulsion while stirring to form a coarse emulsion of microcapsules. Microcapsules of average volume particle size (Dv 0.5) 3.62 micrometers were produced in suspension.

Example 6

Comparative 700 g EHMC (Parsol MCX®) was emulsified in 1080.8 g water containing 2.8 g Pareth-3 nonionic polyethylene glycol lauryl ether surfactant and 1.8 g cetyl trimethyl ammonium chloride (CTAC) cationic surfactant. CTAC/EHMC ratio was then 0.25%. The coarse emulsion was passed once through an "Rannie Mini Lab 8.30H" homogeniser operating at 900 bars (90 MPa). 13.14% TEOS was added to the emulsion while stirring to form a coarse emulsion of microcapsules. Microcapsules of average volume particle size (Dv 0.5) 1.07 micrometers were produced in suspension, but had a shell thickness of less than 18 nanometers.

Example 7

Comparative 700 g EHMC (Parsol MCX®) was emulsified in 1080.8 g water containing 2.8 g Pareth-3 nonionic polyethylene glycol lauryl ether surfactant and 1.8 g cetyl trimethyl ammonium chloride (CTAC) cationic surfactant. CTAC/EHMC ratio was then 0.25%. The coarse emulsion was passed once through a "Rannie Mini Lab 8.30H" homogeniser operating at 900 bars (90 MPa). 13.14% TEOS was added to the emulsion while stirring to form a coarse emulsion of microcapsules. Microcapsules of average volume particle size (Dv 0.5) 1.12 micrometers were produced in suspension, but had a shell thickness of less than 18 nanometers.

Example 8

Comparative 350 g EHMC (Parsol MCX®) was emulsified in 541.6 g water containing 1 g Pareth-3 nonionic polyethylene glycol lauryl ether surfactant and 1.13 g cetyl trimethyl ammonium chloride (CTAC) cationic surfactant. CTAC/EHMC ratio was then 0.32%. The coarse emulsion was passed once through an "APV Model 1000" homogeniser operating at 50 bars (5 MPa). 13.14% TEOS was added to the emulsion while stirring to form a coarse emulsion of microcapsules. Microcapsules of average volume particle size (Dv 0.5) 3.4 micrometers were produced in suspension, but had a shell thickness of less than 18 nanometers.

Example 9

Comparative

This example used the process as disclosed in U.S. Pat. No. 6,303,149B1 wherein TEOS is added oil phase (EHMC phase) prior to the emulsification.
276 g EHMC (Parsol MCX®) was mixed with 24 g of TEOS and the blend was emulsified in 230 g water containing 1.6 g cetyl trimethyl ammonium chloride (CTAC) cationic surfactant. CTAC/EHMC ratio was then 0.58%. The coarse emulsion was emulsified using an IKA Ultra-Turrax Basic T25 during 5 minutes at 9600 rpm.
Microcapsules of average volume particle size (Dv 0.5) 4.5 micrometers were produced in suspension.

Example 10

Comparative

This example illustrates the importance of adding TEOS in the water phase and not in the oil phase (EHMC phase) despite correct CTAC/EHMC ratio.
242 g EHMC (Parsol MCX®) was mixed with 24 g of TEOS and the blend was emulsified in 181 g water containing 0.62 g cetyl trimethyl ammonium chloride (CTAC) cationic surfactant. CTAC/EHMC ratio was then 0.26%. The coarse emulsion was emulsified using an IKA Ultra-Turrax Basic T25 during 5 minutes at 9600 rpm. Microcapsules of average volume particle size (Dv 0.5) 6.3 micrometers were produced in suspension.

Example 11

Comparative

This example illustrates the importance of adding TEOS in the water phase and not in the oil phase (EHMC phase) despite of having correct CTAC/EHMC ratio and correct shell thickness. 242 g EHMC (Parsol MCX®) was mixed with 24 g of TEOS and the blend was emulsified in 181 g water containing 0.62 g cetyl trimethyl ammonium chloride (CTAC) cationic surfactant. CTAC/EHMC ratio was then 0.26%. The coarse emulsion was emulsified using an IKA Ultra-Turrax Basic T25 during 5 minutes at 9600 rpm. Microcapsules of average volume particle size (Dv 0.5) 4 micrometers were produced in suspension.

Three reference compositions (references A, B and C) in a standard sun care preparation were prepared.
Reference A contained 5% EHMC, 2% BMDBM, 1.8% OC (Octocrylene)
Reference B contained 5% EHMC
Reference C contained 2% BMDBM, 1.8% OC.
Samples were also prepared containing the corresponding amount of encapsulated EHMC, 2% BMDBM, 1.8% OC. The preparation of the microcapsules containing EHMC, BMDBM, and OC, as described above. The references and the samples containing the microcapsules were then incorporated into a standard topical composition. The components of the tested compositions are summarised in Table 1 and were prepared according to the following procedure: heat parts A) and B) to 85° C. while stirring. Add the additional non-encapsulated UV-A and/or UV-B and/or broad spectrum screen in the desired concentrations, based on their solubility, to the water or the oil phase. When homogeneous, add part B) to A) under agitation. Cool down to 45° C. while stirring, then add part C). Cool to ambient temperature while stirring. Homogenise again to achieve a small particle size.

The photostability of a suspension was determined and evaluated as described above. The recovery of EHMC and BMDBM in a sample had to be equal to that of the reference B and C in order to prove efficient retention. If the values decreased with time, or were equal to the values of reference A, the retention of the sunscreen agent in the microcapsule is considered insufficient. The compositions were stored at 43° C. to accelerate the aging process.

TABLE 1

| | Formula | Reference A % | Reference B % | Reference C % | Sample |
|---|---|---|---|---|---|
| A) | Glyceryl Myristate | 3 | 3 | 3 | 3 |
| | BMDBM | 2 | — | 2 | 2 |
| | EHMC | 5 | 5 | — | — |
| | OC | 1.8 | — | 1.8 | 1.8 |
| | Cetyl Alcohol | 1 | 1 | 1 | 1 |
| | 200 Fluid 350 cSt | 2 | 2 | 2 | 2 |
| | Tegosoft TN | 14 | 14 | 14 | 14 |
| | Amphisol A | 2 | 2 | 2 | 2 |
| | BHT | 0.05 | 0.05 | 0.05 | 0.05 |
| B) | EDTA BD | .1 | .1 | .1 | .1 |
| | Phenonip | .6 | .6 | .6 | .6 |
| | Tris 25% sol. | 1.3 | 1.3 | 1.3 | 1.3 |
| | Water | 60.15 | 60.15 | 60.15 | 60.15 |
| | Propylene Glycol | 5 | 5 | 5 | 5 |
| | Carbopol ETD 2001 | 0.3 | 0.3 | 0.3 | 0.3 |
| | Tris 25% sol. | 2.5 | 2.5 | 2.5 | 2.5 |
| C) | Encapsulated EHMC | — | — | — | Add 5% Encapsulated EHMC |
| | | 100 | 100 | 100 | 100 |

Shell thicknesses was determined by the following:

$$\text{Shell Thickness (nm)} = [(PS/2) - (PS/2)*(\text{Payload}/100)^{1/3}]*1000$$

where PS is particle size (Dv 0.5) expressed in micrometers
payload=Volume sunscreen agent*100/(Volume sunscreen agent+Volume shell)
Volume sunscreen agent=Weight EHMC/1.011
Volume shell=Weight shell/2

Particle size measurements were made by laser diffraction technique using a "Mastersizer 2000" from Malvern Instruments Ltd., UK. (Further information on the particle size determination can be found in *"Basic Principles of Particle Size Analytics"*, Dr. Alan Rawle, Malvern Instruments Limited, WR14 1XZ, UK and the *"Manual of Malvern Particle Size Analyser"*. Particular reference is made to the user manual number MNA 0096, Issue 1.0, November 1994. All particle sizes indicated in the present application are mean average particle size according to D(v, 0.5) and are measured with a Malvern Mastersizer.

TABLE 2

| | Shell Thickness (nm) | Measurement after | Recovery after irradiation* EHMC (%) | Recovery after irradiation* BMDBM (%) |
|---|---|---|---|---|
| Reference A | NA | initial | 42 | 21 |
| | | 1 week at 43° C. | 44 | 22 |
| | | 2 weeks at 43° C. | 39 | 19 |
| | | 4 weeks at 43° C. | 41 | 23 |
| Reference B | NA | initial | 60 | — |
| | | 1 week at 43° C. | 62 | — |
| | | 2 weeks at 43° C. | 59 | — |
| | | 4 weeks at 43° C. | 61 | — |
| Reference C | NA | initial | — | 66 |
| | | 1 week at 43° C. | — | 67 |
| | | 2 weeks at 43° C. | — | 62 |
| | | 4 weeks at 43° C. | — | 65 |
| Example 1 | 19.3 | initial | 53 | 55 |
| | | 1 week at 43° C. | n.d. | n.d. |
| | | 2 weeks at 43° C. | n.d. | n.d. |
| | | 4 weeks at 43° C. | n.d. | n.d. |
| Example 2 | 22.2 | initial | n.d. | n.d. |
| | | 1 week at 43° C. | 55 | 54 |
| | | 2 weeks at 43° C. | 48 | 48 |
| | | 4 weeks at 43° C. | 51 | 47 |
| Example 3 | 24.9 | initial | n.d. | n.d. |
| | | 1 week at 43° C. | 45 | 43 |
| | | 2 weeks at 43° C. | 47 | 44 |
| | | 4 weeks at 43° C. | 47 | 44 |
| Example 4 | 26.3 | initial | n.d. | n.d. |
| | | 1 week at 43° C. | 53 | 50 |
| | | 2 weeks at 43° C. | 48 | 42 |
| | | 4 weeks at 43° C. | 52 | 45 |
| Example 5 | 22.9 | initial | n.d. | n.d. |
| | | 1 week at 43° C. | 49 | 49 |
| | | 2 weeks at 43° C. | 49 | 47 |
| | | 4 weeks at 43° C. | 50 | 46 |

TABLE 2-continued

| | Shell Thickness (nm) | Measurement after | Recovery after irradiation* EHMC (%) | Recovery after irradiation* BMDBM (%) |
|---|---|---|---|---|
| Example 6 | 13.1 | initial | n.d. | n.d. |
| | | 1 week at 43° C. | 43 | 34 |
| Example 7 | 13.7 | initial | n.d. | n.d. |
| | | 1 week at 43° C. | 46 | 32 |
| Example 8 | 13.7 | initial | n.d. | n.d. |
| | | 1 week at 43° C. | 31 | 17 |
| Example 9 | 9.3 | initial | 73 | 69 |
| | | 1 week RT | 69 | 65 |
| | | 3 weeks RT | 53 | 48 |
| | | 5 months at 43° C. | 64 | 54 |
| Example 10 | 15 | initial | 72 | 67 |
| | | 1 week RT | 71 | 64 |
| | | 3 weeks RT | 68 | 54 |
| | | 5 months at 43° C. | 66 | 56 |
| Example 11 | 28.2 | initial | 69 | 73 |
| | | 1 week RT | 73 | 75 |
| | | 3 weeks RT | 65 | 61 |

*measured by UV absorption of irradiated samples vs. non-irradiated sample

The invention claimed is:

1. A method for controlling the shell thickness of microcapsules greater than or equal to 18 nanometers, wherein the microcapsules are prepared by
   I) mixing an oil phase and an aqueous solution of a cationic surfactant to form an oil in water emulsion,
   II) adding a water reactive silicon compound comprising a tetraethoxysilane to the oil in water emulsion,
   III) polymerizing the tetraethoxysilane at the oil/water interface of the emulsion to form microcapsules having a core containing the oil and a shell,
   said method comprises:
   (i) selecting the weight % of cationic surfactant to the oil phase in the emulsion of step I) ranges from 0.1% to 0.3%, and
   (ii) selecting the oil phase, the amount of the oil phase, and the amount of tetraethoxysilane used in the process so that the thickness of the resulting microcapsules satisfies the following equation:

$$PS \geq (18*2/1000)*1/[1-(\text{Payload}/100)^{1/3}]$$

where PS is particle size (Dv 0.5) expressed in micrometers;
   payload=Volume oil phase*100/(Volume oil phase+Volume shell);
   Volume oil phase=Mass oil phase/density of oil phase; and
   Volume shell=Mass tetraethoxysilane*0.288/2.

2. The process of claim 1 wherein the oil phase contains a sunscreen.

3. The process of claim 2 wherein the sunscreen is ethylhexyl methoxycinnamate.

4. The process of claim 1 wherein the cationic surfactant is cetyl trimethyl ammonium chloride.

* * * * *